US007473673B2

(12) United States Patent
Polonka et al.

(10) Patent No.: US 7,473,673 B2

(45) **Date of Patent: *Jan. 6, 2009**

(54) HYDROPHILIC STRUCTURED BAR COMPOSITIONS COMPRISING INDIVIDUALLY COATED FLAT PLATY PARTICLES, EACH HAVING SURFACE DEPOSITION CHEMISTRY MECHANISM

(75) Inventors: Jack Polonka, Peekskill, NY (US); Joseph Oreste Carnali, Newtown, CT (US); Pravin Shah, Rutherford, NJ (US); Rajesh Patel, Middlebury, CT (US); Georgia Shafer, Southbury, CT (US); Teanoosh Moaddel, Watertown, CT (US)

(73) Assignee: Conopco, Inc., Greenwich, CT (US)

( * ) Notice: Subject to any disclaimer, the term of this patent is extended or adjusted under 35 U.S.C. 154(b) by 38 days.

This patent is subject to a terminal disclaimer.

(21) Appl. No.: 11/370,267

(22) Filed: Mar. 7, 2006

(65) Prior Publication Data

US 2007/0213245 A1 Sep. 13, 2007

(51) Int. Cl.
*A61K 7/50* (2006.01)

(52) U.S. Cl. ...................... 510/141; 510/151; 510/152; 510/153; 510/155; 510/156

(58) Field of Classification Search ...................... None
See application file for complete search history.

(56) References Cited

U.S. PATENT DOCUMENTS

| | | | |
|---|---|---|---|
| 5,296,159 | A | 3/1994 | Wilson et al. |
| 6,780,826 | B2 | 8/2004 | Zhang et al. |
| 2004/0048758 | A1 | 3/2004 | Zhang et al. |
| 2004/0223993 | A1 | 11/2004 | Clapp et al. |

FOREIGN PATENT DOCUMENTS

| | | | |
|---|---|---|---|
| WO | 2005/094780 | A1 | 10/2005 |
| WO | 2005/095571 | A1 | 10/2005 |

OTHER PUBLICATIONS

Polonka et al., U.S. Appl. No. 11/370,109, filed Mar. 7, 2006, Hydrophilic Structured Predominantly Soap-Based Bar Composition Comprising Individually Coated Flat Platy Particles, each having Surface Deposition Chemistry Mechanism.

*Primary Examiner*—Necholus Ogden, Jr.
(74) *Attorney, Agent, or Firm*—Ronald A. Koatz

(57) ABSTRACT

The invention relates to both compositions comprising flat platy particles wherein the particles individually have deposition system (i.e., cationic polymers and anionic surfactant) on them.

17 Claims, 5 Drawing Sheets

HYDROPHILIC STRUCTURED BAR COMPOSITIONS COMPRISING INDIVIDUALLY COATED FLAT PLATY PARTICLES, EACH HAVING SURFACE DEPOSITION CHEMISTRY MECHANISM

FIELD OF THE INVENTION

The present invention relates to bar compositions comprising reflective platy optical materials. More particularly, each of the individual platy particles has a surface deposition chemistry mechanism (e.g., coating or film of cationic polymer and anionic surfactant formed in situ on substantially each individual particle) which allows the particles to attach individually and form a foam-particle structure (e.g., where coated deposition system helps particles attach to surface of foam bubbles), and to be independent of any more generalized deposition system (e.g., such as flocculating surfactant-cationic polymer systems where polymer and anionic surfactant form flocculates which carry non coated particles on the floc, thereby aiding deposition). Deposition occurs predominantly (>50% of original particles) from foam/particles in the foam portion of a foam and liquor which forms during rinse/dilution. Enhanced deposition, independent of a generalized, "carrier" flocculating deposition system, allows the formulation of bars which demonstrate radiant luminosity through the deposition of reflective flat optical material during the cleansing process.

The actual formulations of the bar is also an important factor in whether flocculation will be avoided. In a preferred embodiment of the subject invention, the composition comprises 20 to 80% hydrophilic structurant in combination with 5 to 60% non-soap surfactant (although broadly, amounts of surfactant, soap and non-soap; and of structurant are as defined). In a co-pending application filed on the same date, the bar composition is predominantly soap (e.g., 40 to 90% by wt. soap) and less hydrophilic structurant may be used (e.g., preferably 0.1 to 40%). The composition may also comprise 0-30% synthetic, non-soap detergent.

BACKGROUND

The delivery from bars of enhanced visual benefits to the skin using particulate optical modifier is disclosed, for example, in applicants co-pending application entitled "Beauty Wash Product Bar Compositions Delivering Enhanced Visual Benefits To The Skin with Specific Optical Attributes" filed Jan. 25, 2005.

In that reference, there is no teaching or suggestion that desired optical particles can individually attach directly to foam bubbles (e.g., through deposition chemistry on individual particles rather than a more generalized floc system in which flocs carry multiple particles), and that these particles deposit when lather/particle structures formed from the coated particles attaching to bubbles (foam) contact skin or other substrate (e.g., in rinse) independent of whether or not a floc deposition system is present. Dependent claims in that reference in fact recite that cationic polymer and anionic surfactant will precipitate and that this precipitate may be a floc. Also, there is no distinction in the reference as to the shape of particles and it is clear from the reference that particles may be spheroidal, platy or cylindrical. Also, there is nothing specific about the bar formulation and what may or may not trigger flocculation (e.g., certain amounts of hydrophilic structurant and/or soap).

By contrast, the particles of the subject invention must be flat (e.g., platy) and must be capable of attaching to bubbles/ foam so that they will deposit from the lather/particle structure so formed directly rather than be dependent on a deposition system for deposition. Thus, deposition systems (e.g., anionic surfactant-cationic polymers) are not excluded from this invention. However, the mechanism of particle deposition is not primarily through floc and carry, but through deposition of individual particles from particle-lather structure.

U.S. Pat. No. 6,780,826 to Zhang discloses platy particles similar to those of the invention. However, this reference fails to disclose the required deposition chemistry and further does not recognize that bar formulation (amount of hydrophilic structurant, whether predominantly soap) is also important.

U.S. 2004/0223993 to Clapp disclose particles which are hydrophobically modified for incorporation into a large drop oil phase leading to enhanced deposition. Particles of the subject application are part of a deposition chemistry (e.g., where anionic surfactant and cationic polymer coat particle individually), and are not part of a large drop oil phase (e.g., where deposition is dependent on incorporation of particle into large oil drops).

The foam/particle structure of the subject invention is important in determining that most particles deposit from the foam portion rather than the liquor portion of the rinse (these fractions are formed in use during rinse) because, when delivered primarily by lather contact rather than by direct contact (deposition from floc), there is not deposition in crevices (e.g., of the palm of the hands) which is often perceived as negative by consumers.

BRIEF DESCRIPTION OF THE INVENTION

The present invention provides, in particular, bar compositions comprising:

(1) 5% to 90% by wt., preferably 10 to 60%, more preferably 12 to 30% by wt. of surfactant selected from the group consisting of anionic, nonionic, amphoteric, and cationic surfactants and mixtures thereof; bars of the invention should preferably have at least 25% anionic surfactant (i.e., anionic should comprise at least 25%, preferably at least 50% of the surfactant system). In one embodiment, claimed in separate co-pending application, the bars should comprise 40 to 90% fatty acid soap (e.g., 40 to 90% of total composition);

(2) 0.1% to 80%, preferably 20 to 70% by wt. of hydrophilic water-soluble or water insoluble hydrophilic structurant (e.g., PEG, starches etc.); when composition is a predominantly soap-based composition (e.g., comprises 40-90% soap), levels of structurant are generally on lower order, e.g., 1.0 to 40%, preferably 2 to 30%, more preferably 2 to 25%;

(3) 0.1 to 20%, preferably 0.2 to 10% by wt. of a deposition enhancement system (e.g., cationic polymer, and anionic surfactant which can precipitate when combined with the cationic polymer);

wherein molecule or molecules forming said deposition enhancement system form an individual coating in situ on about 50% to 100%, preferably at least 60% of particles of (5) below, such that said individually coated particles attach individually to bubbles formed during rinse (foam/particle) allowing particles to deposit by lather contact from the foam particle structures as formed;

(4) 0 to 10%, preferably 0.1 to 5% by wt. emollient, wherein said emollient is deposited through the individualized in situ coatings (preferably), and/or through any more "generalized" deposition that may be present in the formulation;

(5) 0.1 to 15%, preferably 0.5 to 10% by wt. of solid particulate optical modifier wherein said modifier is flat, platy particulate having $D_{50}$ size range (e.g., median of particle size distribution) of 6 to 70 micrometer and thickness of 50 to 1000 nanometer; and (6) 1 to 20%, preferably 5 to 18% by wt. water;

wherein from at least 50 to 100% of said platy particles deposit predominately from surface of foam (foam/particle) generated during rinse (e.g., due to their deposition chemistry defined by (3) above);

said foam-platy particle structure delivering sensory moisturization feel (measured by Theological measurements of foam, i.e., foam lather; and/or by post-tactile sensory acoustical data).

In a preferred embodiment of this invention, the composition comprise 5 to 60% non-soap surfactant and 20 to 80% hydrophilic structurant. In co-pending application, filed on same date, invention is directed to soap based bars which more preferably comprise 40 to 90% soap and 0.1 to 40% hydrophilic surfactant.

Because the optical particles are delivered from a foam particle structure, they provide both a visual effect (from the particles) and a moisturizing effect (from foam sensory effect). Thus, the flat platy particles have dual use sensory effect (i.e., optical and moisturizing).

These and other aspects, features and advantages will become apparent to those of ordinary skill in the art from a reading of the following detailed description and the appended claims. For the avoidance of doubt, any feature of one aspect of the present invention may be utilized in any other aspect of the invention. It is noted that the examples given in the description below are intended to clarify the invention and are not intended to limit the invention to those examples per se. Other than in the experimental examples, or where otherwise indicated, all numbers expressing quantities of ingredients or reaction conditions used herein are to be understood as modified in all instances by the term "about". Similarly, all percentages are weight/weight percentages of the total composition unless otherwise indicated. Numerical ranges expressed in the format "from x to y" are understood to include x and y. When for a specific feature multiple preferred ranges are described in the format "from x to y", it is understood that all ranges combining the different endpoints are also contemplated. Where the term "comprising" is used in the specification or claims, it is not intended to exclude any terms, steps or features not specifically recited. All temperatures are in degrees Celsius (° C.) unless specified otherwise. All measurements are in SI units unless specified otherwise. All documents cited are—in relevant part—incorporated herein by reference.

DETAILED DESCRIPTION OF THE INVENTION

Figure 1:
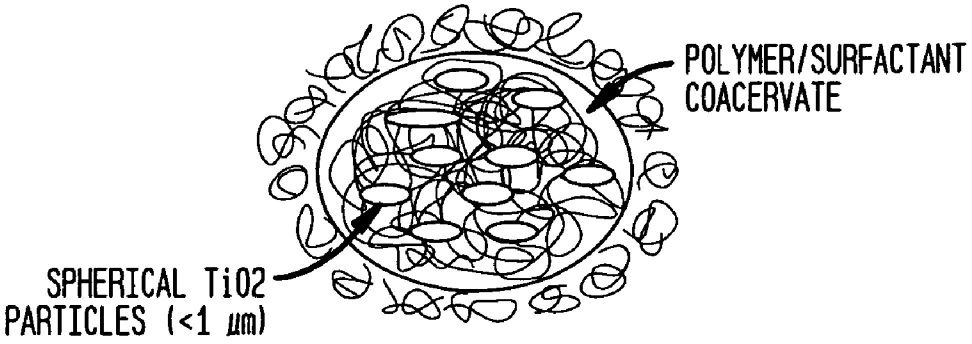
FIG. 1 is a schematic representation of what occurs when non-platy material (e.g., $TiO_2$) is used in combination with deposition enhancement system. As noted, flocculation occurs and optical modifier is presumably delivered through flocs (not individually).
Figure 2:
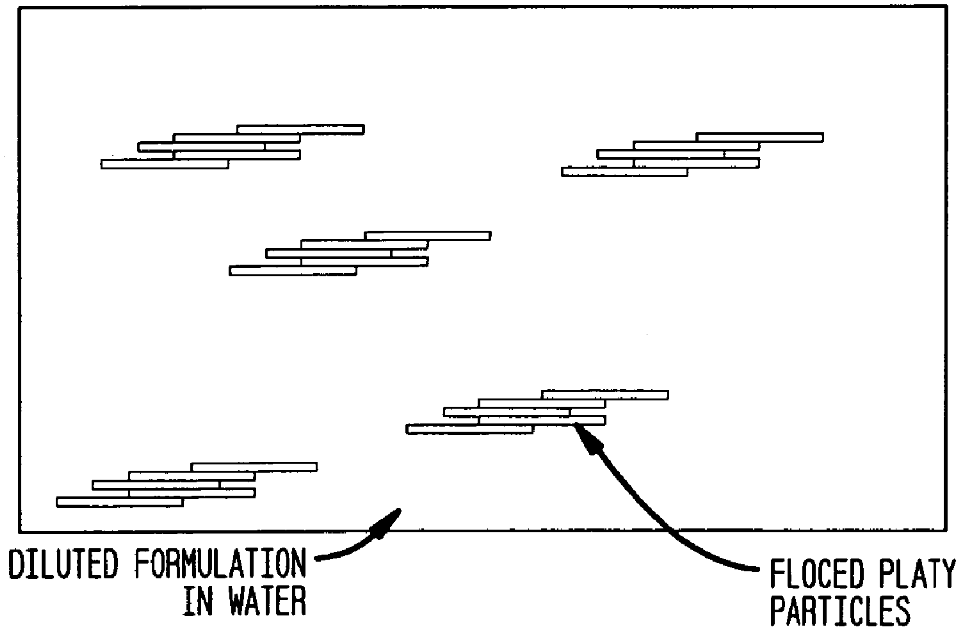
FIG. 2 is schematic of what occurs when platy material (i.e., TCM) is used in combination with deposition enhancement system. The particles are clumped in this figure.
Figure 4:
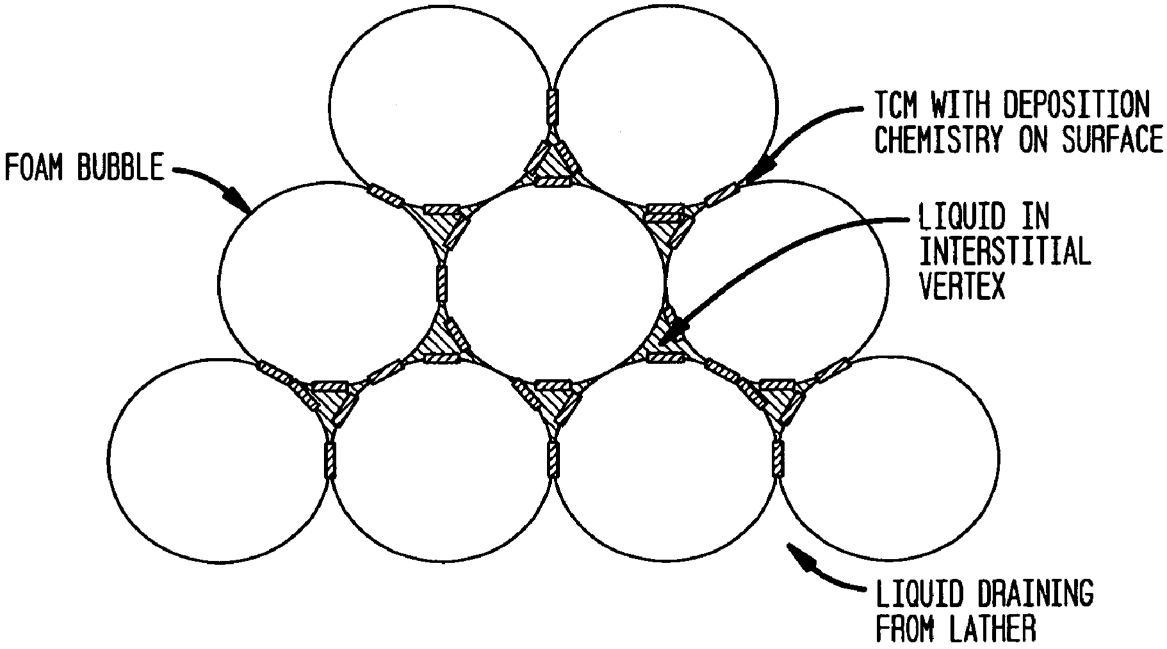
FIG. 4 is schematic of foam particle deposition system where substantially all particles (e.g., >50%, preferably >60%) are delivered through foam bubbles rather than through floc deposition system.

The present invention relates to bar compositions comprising platy particulate particles wherein said particles form a foam-platy particle structure during rinse such that a predominance (>50%, preferably >60%, e.g., 60-100% or 60 to 95%) of such particles are delivered to the skin from the foam-particle structure (FIG. 4) rather than from a floc deposition system (FIGS. 1 and 2). Preferably less than 20%, more preferably less than 15%, even more preferably less than 10% of particles are delivered through flocculation. It is possible no particles are delivered through flocculation at all.

The delivery from foam-particle structures not only permits delivery of visual effect (from the particles), but also creates a moisturizing sensation simultaneous with delivery of the optical effect.

In a second embodiment of the invention, the invention relates to a process for delivering a dual optical (e.g., brightening) and moisturizing effect by using bar compositions as defined above and subsequently rinsing with water.

The invention is defined in greater detail as noted below.

In general, the surfactant system of the invention used is also not critical. It is, however, preferred that there be present at least one lathering anionic surfactant. Preferably such anionic should comprise at least 25% of the total surfactant concentration.

Broadly, surfactant is present at level of 5 to 90%, preferably 10 to 60% by wt. of composition.

In general, the surfactant is selected from the group consisting of soap (including pure soap systems), anionic surfactant, nonionic surfactant, amphoteric/zwitterionic surfactant, cationic surfactant and mixtures thereof. As noted below, when a predominantly soap system is used (40-90% by wt. composition), generally less hydrophilic structurant (e.g., 0.1 to 40%) is required for individual coated particle effect.

Non-limiting examples of anionic surfactants are disclosed in McCutcheon's Detergents and Emulsifiers, North American Edition (1986), published by Allured Publishing Corporation; McCutcheon's Functional materials, North Americas Edition (1992), both of which are incorporated by reference into the subject application.

Examples of anionic surfactants include sarcosinates, sulfates, isethionates, glycinates, taurates, phosphates, lactylates, glutamates and mixtures thereof. Among isethionates are preferred alkoxyl isethionates such as sodium cocoyl isethionate, sodium lauroyl isethionate and mixtures.

The alkyl and alkyl ether sulfates typically have the respective formulae $ROSO_3M$ and $RO(C_2H_4O)_xSO_3M$, wherein R is alkyl or alkenyl of from about 10 to about 30 carbon atoms, x is from about 1 to about 10, and M is a water-soluble cation such as ammonium, sodium, potassium, magnesium and triethanolamine. Another suitable class of anionic surfactants are the water-soluble salts of the organic, sulfuric acid reaction products of the general formula:

$R_1—SO_3—M$ wherein $R_1$ is chosen from the group consisting of a straight or branched chain, saturated aliphatic hydrocarbon of radical having from about 8 to about 24, preferably about 10 to about 16, carbon atoms; and M is a cation. Still other anionic synthetic surfactants include the class designated as succinamates, olefin sulfonates having about 12 to about 24 carbon atoms, and alkyloxy alkane sulfonates. Examples of these materials are sodium lauryl sulfate and ammonium lauryl sulfate.

Other anionic materials useful herein are soaps (i.e., alkali metal salts, e.g., sodium or potassium salts or ammonium or triethanolamine salts) of fatty acids, typically having from about 8 to about 24 carbon atoms, preferably from about 10 to about 20 carbon atoms. The fatty acids used in making the soaps can be obtained from natural sources such as, for instance, plant or animal-derived glycerides (e.g., palm oil, coconut oil, soybean oil, castor oil, tallow, lard, etc.). The fatty acids can also be synthetically prepared. Soaps are described in more detail in U.S. Pat. No. 4,557,853. In a preferred embodiment of the present invention, the compositions are predominantly synthetic non-soap, or low soap (generally less than about 1%, and less than amount of non-soap surfactant) compositions with 20-80% hydrophilic structurant, while an accompanying application filed by applicants is concerned with predominantly soap-based compositions (40 to 90% soap). Such compositions generally comprise 0.1 to 40% hydrophilic structurant.

Other useful anionic materials include phosphates such as monoalkyl, dialkyl, and trialkylphosphate salts.

Other anionic materials include alkanoyl sarcosinates corresponding to the formula $RCON(CH_3)CH_2CH_2CO_2M$ wherein R is alkyl or alkenyl of about 10 to about 20 carbon atoms, and M is a water-soluble cation such as ammonium, sodium, potassium and alkanolamine (e.g., triethanolamine), a preferred examples of which are sodium lauroyl sarcosinate, sodium cocoyl sarcosinate, ammonium lauroyl sarcosinate, and sodium myristoyl sarcosinate. TEA salts of sarcosinates are also useful.

Also useful are taurates which are based on taurine, which is also known as 2-aminoethanesulfonic acid. Especially useful are taurates having carbon chains between $C_8$ and $C_{16}$. Examples of taurates include N-alkyltaurines such as the one prepared by reacting dodecylamine with sodium isethionate according to the teaching of U.S. Pat. No. 2,658,072 which is incorporated herein by reference in its entirety. Further non-limiting examples include ammonium, sodium, potassium and alkanolamine (e.g., triethanolamine) salts of lauroyl methyl taurate, myristoyl methyl taurate, and cocoyl methyl taurate.

Also useful are lactylates, especially those having carbon chains between $C_8$ and $C_{16}$. Non-limiting examples of lactylates include ammonium, sodium, potassium and alkanolamine (e.g., triethanolamine) salts of lauroyl lactylate, cocoyl lactylate, lauroyl lactylate, and caproyl lactylate.

Also useful herein as anionic surfactants are alkylamino carboxylates such as glutamates, especially those having carbon chains between $C_8$ and $C_{16}$. Non-limiting examples of glutamates include ammonium, sodium, potassium and alkanolamine (e.g., triethanolamine) salts of lauroyl glutamate, myristoyl glutamate, and cocoyl glutamate.

Non-limiting examples of preferred anionic lathering surfactants useful herein include those selected from the group consisting of sodium lauryl sulfate, ammonium lauryl sulfate, ammonium laureth sulfate, sodium laureth sulfate, sodium trideceth sulfate, ammonium cetyl sulfate, sodium cetyl sulfate, ammonium cocoyl isethionate, sodium lauroyl isethionate, sodium lauroyl lactylate, triethanolamine lauroyl lactylate, sodium caproyl lactylate, sodium lauroyl sarcosinate, sodium myristoyl sarcosinate, sodium cocoyl sarcosinate, sodium lauroyl methyl taurate, sodium cocoyl methyl taurate, sodium lauroyl glutamate, sodium myristoyl glutamate, and sodium cocoyl glutamate and mixtures therefor.

Especially preferred for use herein is ammonium lauryl sulfate, ammonium lauryl ether sulfate, sodium lauryl ether sulfate, sodium lauroyl sarcosinate, sodium cocoyl sarcosinate, sodium myristoyl sarcosinate, sodium lauroyl lactate, and triethanolamine lauroyl lactylates.

Nonionic Lathering Surfactants

Non-limiting examples of nonionic lathering surfactants for use in the compositions of the present invention are disclosed in McCutcheon's, Detergents and Emulsifiers, North American Edition (1986), published by allured Published Corporation; and McCutcheon's, Functional materials, North American Edition (1992); both of which are incorporated by reference herein in their entirety.

Nonionic lathering surfactants useful herein include those selected form the group consisting of alkyl glucosides, alkyl polyglucosides, polyhydroxy fatty acid amides, alkoxylated fatty acid esters, alcohol ethoxylates, lathering sucrose esters, amine oxides, and mixtures thereof.

Alkyl glucosides and alkylipolyglucosides are useful herein, and can be broadly defined as condensation articles of long chain alcohols, e.g., C8-30 alcohols, with sugars or starches or sugar or starch polymers i.e., glycosides or polyglycosides. These compounds can be represented by the formula $(S)_n$—O—R wherein S is a sugar moiety such as glucose, fructose, mannose, and galactose; is an integer of from about 1 to about 1000, and R is a C8-30 alkyl group. Examples of long chain alcohols from which the alkyl group can be derived include decyl alcohol, cetyl alcohol, stearyl alcohol, lauryl alcohol, myristyl alcohol, oleyl alcohol and the like. Preferred examples of these surfactants include those wherein S is a glucose moiety, R is a C8-20 alkyl group, and n is an integer of from about 1 to about 9. Commercially available examples of these surfactants include decyl polyglucoside (available as APG 325 CS from Henkel) and lauryl polyglucoside (available as APG 600 CS and 625 CS from Henkel). Also useful are sucrose ester surfactants such as sucrose cocoate and sucrose laurate.

Other useful nonionic surfactants include polyhydroxy fatty acid amide surfactants, more specific examples of which include glucosamides, corresponding to the structural formula:

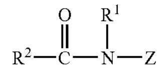

wherein $R^1$ is H, $C_1$-$C_4$ alkyl, 2-hydroxyethyl, 2-hydroxypropyl, preferably $C_1$-$C_4$ alkyl, more preferably methyl or ethyl, most preferably methyl; $R^2$ is $C_5$-$C_{31}$ alkyl or alkenyl, preferably $C_7$-$C_{19}$ alkyl or alkenyl, more preferably $C_9$-$C_{17}$ alkyl or alkenyl, most preferably $C_{11}$-$C_{15}$ alkyl or alkenyl; and Z is a polyhydroxy hydrocarbyl moiety having a linear hydrocarbyl chain with at least 3 hydroxyl directly connected to the chain, or an alkoxylated derivative (preferably ethoxylated or propoxylated) thereof. Z preferably is a sugar moiety selected from the group consisting of glucose, fructose, maltose, lactose, galactose, mannose, xylose, and mixtures thereof. As especially preferred surfactant corresponding to the above structure is coconut alkyl N-methyl glucoside amide (i.e., wherein the $R^2CO$-moiety is derived form coconut oil fatty acids).

Other examples of nonionic surfactants include amine oxides. Amine oxides correspond to the general formula $R_1R_2R_3NO$, wherein $R_1$ contains an alkyl, alkenyl or monohydroxyl alkyl radical of from about 8 to about 18 carbon atoms, from 0 to about 10 ethylene oxide moieties, and from 0 to about 1 glyceryl moiety, and $R_2$ and $R_3$ contain from about 1 to about 3 carbon atoms and from 0 to about 1 hydroxy group, e.g., methyl, ethyl, propyl, hydroxyethyl, or hydroxypropyl radicals. The arrow in the formula is a conventional representation of a semipolar bond. The examples of amine oxides suitable for use in this invention include dimethyldodecylamine oxide, 2-dodecoxyethyldimethylamine oxide, and dimethylhexadecyclamine oxide.

Non-limiting examples of preferred nonionic surfactants for use herein are those selected form the group consisting of C8-C14 glucose amides, C8-C14 alkyl polyglucosides, sucrose cocoate, sucrose laurate, lauramine oxide, cocoamine oxide, and mixtures thereof.

Amphoteric Lathering Surfactants

The term "amphoteric lathering surfactant," as used herein, is also intended to encompass zwitterionic surfactants, which are well known to formulators skilled in the art as a subset of amphoteric surfactants.

A wide variety of amphoteric lathering surfactants can be used in the compositions of the present invention. Particularly useful are those which are broadly described as derivatives of aliphatic secondary and tertiary amines, preferably wherein the nitrogen is in a cationic state, in which the aliphatic radicals can be straight or branched chain and wherein one of the radicals contains an ionizable water solubilizing group, e.g., carboxy, sulfonate, sulfate, phosphate, or phosphonate.

Non-limiting examples of amphoteric surfactants useful in the compositions of the present invention are disclosed in McCutcheon's, Detergents and Emulsifiers, North American Edition (1986), published by Allured Publishing Corporation; and McCutcheon's, Functional Materials, North American Edition (1992); both of which are incorporated by reference herein in their entirety.

Non-limiting examples of amphoteric or zwitterionic surfactants are those selected from the group consisting of betaines, sultaines, hydroxysultaines, alkyliminoacetates, iminodialkanoates, aminoalkanoates, and mixtures thereof.

Examples of betaines include the higher alkyl betaines, such as coco dimethyl carboxymethyl betaine, lauryl dimethyl carboxymethyl betaine, lauryl dimethyl alphacarboxyethyl betaine, cetyl dimethyl carboxymethyl betaine, cetyl dimethyl betaine (available as Lonaine 16SP from Lonza Corp.), lauryl bis-(2-hydroxyethyl) carboxymethyl betaine, oleyl dimethyl gamma-carboxypropyl betaine, lauryl bis-(hydroxypropyl)alpha-carboxyethyl betaine, coco dimethyl sulfopropyl betaine, lauryl dimethyl sulfoethyl betaine, lauryl bis-(2-hydroxyethyl) sulfopropyl betaine, amidobetaines and amidosulfobetaines (wherein the $RCONH(CH_2)3$ radical is attached to the nitrogen atom of the betaine), oleyl betaine (available as amphoteric Velvetex OLB-50 from Henkel), and cocamidopropyl betaine (available as Velvetex BK-35 and BA-35 from Henkel).

Example of sultaines and hydroxysultaines include materials such as cocamidopropyl hydroxysultaine (available as Mirataine CBS from Rhone-Poulenc).

Preferred amphoteric surfactants having the following structure:

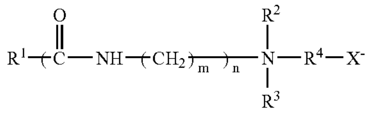

wherein $R^1$ is unsubstituted, saturated or unsaturated, straight or branched chain alkyl having from about 9 to about 22 carbon atoms. Preferred $R^1$ has from about 11 to about 18 carbon atoms; more preferably from about 12 to about 18 carbon atoms; more preferably still from about 14 to about 18 carbon atoms; m is an integer from 1 to about 3, more preferably from about 2 to about 3, and more preferably about 3; n is either 0 or 1, preferably 1; $R^2$ and $R^3$ are independently selected from the group consisting of alkyl having from 1 to about 3 carbon atoms, unsubstituted or mono-substituted with hydroxy, preferred $R^2$ and $R^3$ are $CH_3$; X is selected form the group consisting of $CO_2$, $SO_3$ and $SO_4$; $R^4$ is selected form the group consisting of saturated or unsaturated, straight or branched chain alkyl, unsubstituted or mono-substituted with hydroxy, having from 1 to about 5 carbon atoms. When X is $CO_2$, $R^4$ preferably has 1 to 3 carbon atoms, more preferably 1 carbon atom. When X is $SO_3$ or $SO_4$, $R^4$ preferably has from about 2 to about 4 carbon atoms, more preferably 3 carbon atoms.

Examples of amphoteric surfactants of the present invention include cetyl dimethyl betaine, cocamidopropylbetaine, and cocamidopropyl hydroxy sultaine Cationic Surfactants Cationic surfactants are another useful class of surfactants that can be employed as auxiliary agents. They are particularly useful as additives to enhance skin feel, and provide skin conditioning benefits. One class of cationic surfactants is heterocyclic ammonium salts such as cetyl or stearyl pyridinium chloride, alkyl amidoethyl pyrrylinodium methyl sulfate, lapyrium chloride.

Tetra alkyl ammonium salts is another useful class of cationic surfactants. Examples include cetyl or stearyl trimethyl ammonium chloride or bromide; hydrogenated palm or tallow trimethylammonium halides; behenyl trimethyl ammonium halides or methyl sulfates; decyl isononyl dimethyl ammonium halides; ditallow (or distearyl) dimethyl ammonium halides; behenyl dimethy ammonium chloride.

Other types of cationic surfactants that can be employed are the various ethoxylated quaternary amines and ester quats. Examples are PEG-5 stearyl ammonium lactate (e.g., Genamin KSL manufactured by Clarion), PEG-2 coco ammonium chloride, PEG-15 hydrogenated tallow ammonium chloride, PEG 15 stearyl ammonium chloride, dialmitoyl ethyl methyl ammonium chloride, dipalmitoyl hydroxyethyl methyl sulfate, strearyl amidopropyl dimethylamine lactate.

Still other useful cationic surfactants are quaternized hydrolysates of silk, wheat, and keratin proteins.

The surfactants, along with cationic polymer, form a coating in situ on the platy particles individually upon dilution or usage of the product. The coated platy particles are then capable of forming a foam particle structure when foam is formed during rinse. It is because of this structure that at least 50%, preferably at least 60% and up to 100% of optical particles are then delivered from foam rather than by typical flocculation deposition.

Structurant

The structurant of the invention can be a water-soluble or water insoluble hydrophilic structurant. In the subject application, structurant forms at least 0.1 to 80% of the composition. In a preferred embodiment of the invention, compositions are predominantly no soap or low-soap compositions comprising 15 to 60% non-soap synthetic surfactants (and less than 15%, preferably less than 10%, preferably less than 5%, preferably less than 1% soap; soap may be absent altogether). For such compositions, structurant is preferably present at 20 to 80%, preferably 30 to 70% by wt.

In soap-based compositions, structurant is preferably present at 0.1 to 40%, preferably 2 to 30%, more preferably 2 to 25% by wt.

Water soluble structurants include moderately high molecular weight polyalkylene oxides of appropriate melting point (e.g. 400 to 100° C., preferably 50° to 90° C.) and in particular polyethylene glycols or mixtures thereof.

Polyethylene glycols (PEG's) which are used may have a molecular weight in the range 50 to 25,000 preferably 100 to 10,000. However, in some embodiments of this invention it is preferred to include a fairly small quantity of polyethylene glycol with a molecular weight in the range from 50,000 to 500,000, especially molecular weights of around 100,000. Such polyethylene glycols have been found to improve the wear rate of the bars. It is believed that this is because their long polymer chains remain entangled even when the bar composition is wetted during use.

If such high molecular weight polyethylene glycols (or any other water soluble high molecular weight polyalkylene oxides) are used, the quantity is preferably from 1% to 5%, more preferably from 1% or 1.5% to 4% or 4.5% by weight of the composition. These materials will generally be used jointly with a large quantity of other water-soluble structurant such as the above mentioned polyethylene glycol of molecular weight 50 to 25,000, preferably 100 to 10,000. If PEGs are used, they should preferably not be used in amounts greater than about 20% by wt. as they may induce flocculation.

Water insoluble hydrophilic structurants also have a melting point in the range 400 to 100° C., more preferably at least 50° C., notably 50° C. to 90° C. Suitable materials which are particularly envisage are fatty acid soaps, particularly those having a carbon chain of 12 to 24 carbon atoms. Examples are soaps, lauric, myristic, palmitic, stearic, arachidic and behenic acids and mixtures thereof. Sources of these fatty acids are coconut, topped coconut, palm, palm kernel, babassu and tallow fatty acids and partially or fully hardened fatty acids or distilled fatty acids. Other suitable water insoluble structurants include alkenols of 8 to 20 carbon atoms, particularly cetyl alcohol. These materials generally have a water solubility of less than 5 g/litre at 20° C. When used in a predominantly soap composition (40-90% soap), the soap functions as both surfactant and structurant. When used in a predominantly synthetic, non-soap or low soap composition, it functions as a structurant and comprises generally less than 15% by wt., preferably less than 10% and may be absent altogether.

The relative proportions of the water-soluble hydrophilic structurants and water insoluble hydrophilic structurants govern the rate at which the bar wears during use. The presence of the water-insoluble structurant tends to delay dissolution of the bar when exposed to water during use and hence retard the rate of wear.

As indicated the structurant is used broadly in the bar in an amount of 0.1% to 80%, preferably 20% to 70% by wt., depending on type of surfactant base.

In a preferred embodiment, the structurant comprises predominantly water-soluble structurant. Hydrophobic structurant (e.g., free fatty acids, wax) should comprise no more than 25%, preferably no more than 10% of structurant system; and such hydrophobic structurant should comprise no more than 25%, preferably less than 20%; more preferably less than 15% by wt. of bar overall.

By water soluble is meant generally that 1% or more of compound is soluble in water at room temperature.

Deposition Enhancement System

Figure 3:
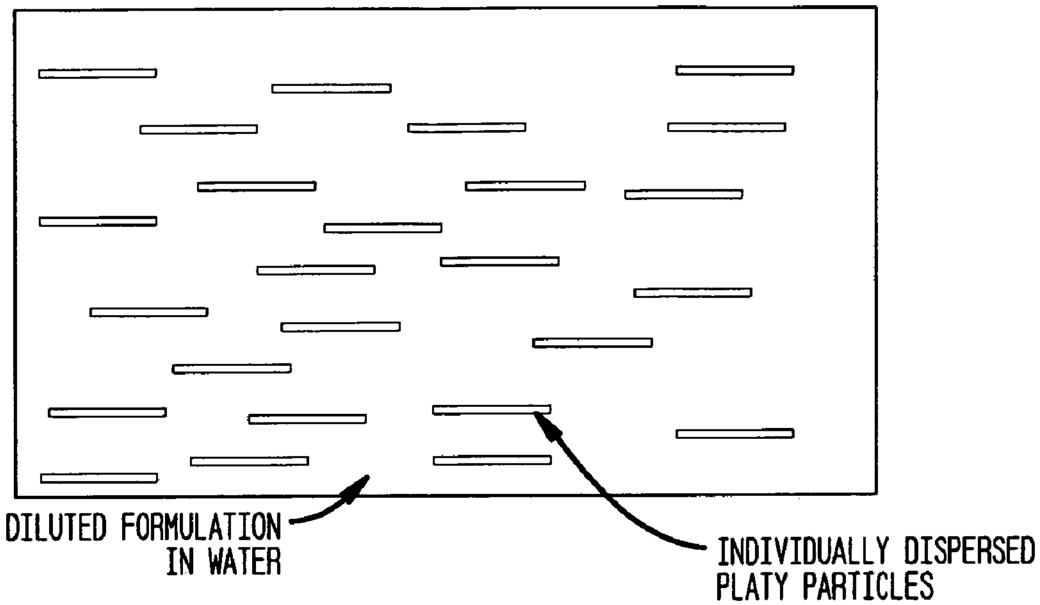
FIG. 3 is a schematic of what occurs when platy material (e.g., titanium dioxide coated mica) is used. There is no obvious floc formation, yet optical modifier is delivered (i.e., through foam/particle deposition). Further, deposition through foam creates moisturization effect.

The deposition enhancement system of the invention, as noted, is unique in that platy optical modifier particles (i.e., predominance, if not all) individually comprise the system (FIG. 3) thereof allowing the particles to deposit from the rinse. That is the platy particles are individually coated, for example, with cationic polymer/anionic surfactant, thereby permitting the particles to attach to the foam and form a particle-foam structure (upon creation of foam on rinse (see FIG. 4)), thereby allowing majority of particles to deposit directly from said rinse. A typical deposition system present in the particles comprises as follows:

a) from about 0.1 to about 10% by wt., preferably 0.1 to 8% by wt. of a cationic polymer, preferably having change density ≧1 Meq/gram, and
b) about 0.1 to 30% by wt., preferably 0.5% to 25% by wt. of an anionic surfactant which forms a precipitate with cationic polymer upon dilution.

Emollient

The deposition system (which deposits on the particle surface during dilution in use) may also comprise 0 to 10%, preferably 0.1 to 10% by wt. emollient although emollient need not be part of the deposition system at all.

Examples of emollients which may be used include glycerin, alkylene glycols (e.g., ethylene or propylene glycol or mixtures thereof) and primary, secondary and/or tertiary amines. A preferred amine is trialkanolamine such as triethanolamine. Another preferred emollient is urea. Mixtures of any or all of the above emollients may be used. Said emollient(s) further aid deposition of the optical modifiers.

As for the deposition system, typically the cationic polymer and anionic surfactant (e.g., anionic surfactant) can form a precipitate on individual particles upon dilution as noted.

Example of surfactants which can be used in the deposition system (whether forming floc or individually attach to each particle) include $C_{10}$-$C_{24}$ fatty acid soaps (e.g., laurates), alkyl taurate (e.g., cocoyl methyl taurate or other alkyl taurates), sulfosuccinates, alkyl sulfates, glycinates, sarcosinates and mixtures thereof.

It is preferred that the cationic have the noted charge in order to form the precipitate. The polymers may be modified polysaccharides including cationic guar gums, synthetic cationic polymers, cationic starches, etc.

Specific cationic polymers which are to be used include Merquat®) polymers such as polyquaternium 6 (e.g., Merquat®100 or Salcare®SC30) and polyquatrnium7 (e.g. Merquat®2200 or Salcare®SC10); guar gums and/or derivatives (e.g. Jaguar C17); quaternized vinylpyrrolidone/methacrylate copolymers (e.g., Gafquat® 775); and polyquaternium-16 (e.g.; Luviquat®FC550).

Specific examples of polymers and their charge densities are disclosed in the Table below:

| Type of Polymer | TradeName | Company | Charge Density (meg/g) |
|---|---|---|---|
| Guar | | | |
| Guar hydroxypropyltrimonium chloride | Jaguar C17 | Rhodia | >Jaguar C13S |
| Hydroxypropyl guar hydroxypropyltrimonium chloride | Jaguar 162 | Rhodia | –Jaguar C13S |
| Guar hydroxypropyltrimonium chloride | Jaguar C13S | Rhodia | 0.8 |
| Guar hydroxypropyltrimonium chloride | Jaguar C14S | Rhodia | ~Jaguar C13S |
| Guar hydroxypropyltrimonium chloride | Jaguar Excel | Rhodia | ~Jaguar C13S |
| Guar hydroxypropyltrimonium chloride | N-Hance 3000 | Hercules | 0.41 |
| Guar hydroxypropyltrimonium chloride | N-Hance 3196 | Hercules | 0.72 |
| Guar hydroxypropyltrimonium chloride | N-Hance 3215 | Hercules | 1.05 |
| Synthetics | | | |
| Polyquaternium-6 | Merquat 100 | Ondeo Nalco | 6.2 |
| Polyquaternium-7 | Merquat 2200 | Ondeo Nalco | 3.1 |
| Polyquaternium-7 | Merquat 550 | Ondeo Nalco | 3.1 |
| Polyquaternium-7 | Merquat S | Ondeo Nalco | 3.1 |
| Polyquaternium-7 | Salcare Super 7 | Ciba | 1.5 |
| Polyquaternium-7 | Salcare SC10 | Ciba | 4.3 |
| Polyquaternium-7 | Salcare SC11 | Ciba | 3.1 |
| Polyquaternium-6 | Salcare SC30 | Ciba | 6.2 |
| Polyquaterniumj-16 | Luviquat FC370 | BASF | 2 |
| Polyquaterniumj-16 | Luviquat FC550 | BASF | 3.3 |
| Polyquaterniumj-16 | Luviquat FC552 | BASF | 3 |
| Polyquaterniumj-16 | Luviquat FC905 | BASF | 6.1 |
| Polyquaternium-44 | Luviquat MS370 | BASF | 1.4 |
| Cationic Cellulose Derivatives | | | |
| Polyquaternium-4 | Celquat H-100 | National Starch | 0.71 |
| Polyquaternium-4 | Celquat L-200 | National Starch | 1.43 |
| Polyquaternium-4 | Celquat SC230M | National Starch | 1.36 |
| Polyquaternium-4 | Celquat SC240C | National Starch | 1.29 |
| Polyquaternium-4 | UCARE Polymer JR | Dow Amerchol | 1.3 |
| Polyquaternium-4 | UCARE Polymer JR | Dow Amerchol | 0.7 |
| Dextran Derivatives | | | |
| Dextran hydroxypropylammonium chloride | CDC | Meito Sangyo | 1.6 |

The deposition system (cationic polymer/anionic surfactant) forms an integral structure with the foam bubbles (on each individual bubble (see FIG. 4)) which, when foam and liquor portions are also formed during rinse, allows foam/particles to deposit from the foam portion (lather deposition) rather than by flocculation from liquor (directly). The deposited particles can be broken by shear/rubbing to form a uniform and dispersed film (comprising optical particles) on surface of substrate. It should be noted that non-platy particles (e.g., pigmentary $TiO_2$) do not form this structure (see FIG. 1).

The oil/emollient, whether or not part of deposition system can be, for example, silicone, castor oil, and sunflower seed oil. Emollient can be deposited through the individualized in situ particle coatings and/or through any more generalized deposition system that may be present.

One example of such particles suspended in oil, for example, is bismuth oxychloride suspended in castor oil (e.g., Rona® Biron Silver, a 70% solids suspension in castor oil).

It should be further noted that oils/emollients may be used which are not specifically associated with deposition and which are added for sensory (e.g., tactile) effect. Among oils which may be used are included, for example, vegetable oils such as orachis oil, castor oil, cocoa butter, coconut oil, corn oil, cotton seed oil, palm kernel oil, rapeseed oil, sunflower seed oil, safflower seed oil, sesame seed oil and soybean oil.

Emollients may include the vegetable oils noted above and may further comprise esters, fatty acids, alcohols, polyols and hydrocarbons. Esters may be mono- or di-esters. Acceptable examples of fatty di-esters include dibutyl adipate, diethyl sebacate, diisopropyl dimerate, and dioctyl succinate. Acceptable branched chain fatty esters include 2-ethyl-hexyl myristate, isopropyl stearate and isostearyl palmitate. Acceptable tribasic acid esters include triisopropyl trilinoleate and trilauryl citrate. Acceptable straight chain fatty esters include lauryl palmitate, myristyl lactate, oleyl eurcate and stearyl oleate. Preferred esters include coco-caprylate and co-caprate, propylene glycol myristyl ether acetate, diisopropyl adipate and cetyl octanoate.

Suitable fatty alcohols and acids include those compounds having from 10 to 20 carbon atoms. Especially preferred are such compounds such as cetyl, myristyl, palmitic and stearyl alcohols and acids.

Among the polyols which may serve as emollients are linear and branched chain alkyl polyhydroxyl compounds. For example, propylene glycol, sorbitol and glycerin are preferred. Also useful may be polymeric polyols such as polypropylene glycol and polyethylene glycol.

The solid particulate optical modifier of the invention comprises 0.5 to 15%, preferably 0.5 to 10% by wt. of the composition. The platy particulate have $D_{50}$ size range of 6 to 70 nanometers and thickeners of 50 to 1000 nanometers.

Broadly, the optical modifier may be defined as follows:

(a) exterior surface with refractive index of 1.3 to 4.0;

(b) thickness of 50 nm to 1,000 nm, preferably 100 nm to 1,000 nm;

(c) $D_{50}$ of 6 to 70 microns in particle size, preferably 14 to 35 microns.

The modifier may be further defined by a color which is obtained by florescence, absorption and/or interference.

As noted, the particles are specific such that they form a particle-foam structure wherein a predominance of such particles will deposit, upon rinse, from the structure.

Examples of such particles include:

i) coated mica or platy organic or inorganic substrate, coated with one or multiple layers of titanium oxide, iron oxide, chromium oxide, metal oxides/mixed metal oxides, nitrides, sulfides, carbides or mixtures thereof;

ii) platy single crystals such as bismuth oxychloride, boron nitride, aluminum oxide, calcium sulfate, iron oxide, mixed metal oxides, metal oxides, nitrides, sulfides, halides, or mixtures thereof.

iii) platy silicate materials (natural or man made) such as mica, talc, sericite, fluoromica, platy silicon oxide, platy borosilicate and platy glass, or mixtures thereof; or iv) a mixture of same or all of the groups above.

These materials may comprise organic and/or inorganic material capable of generating color. The optical particles may further contain surface modification selected from amino acids, proteins, fatty acids, lipids, phospholipids, anionic and/or cationic polymers and mixtures thereof.

Finally, compositions of the invention comprise 1 to 20%, preferably 5 to 18% water.

In a second embodiment, the invention relates to a process for providing dual optical enhancing and moisturizing effect which process comprises using bars of invention and rinsing with water.

The composition of the invention provides change in radiant luminosity wherein delivery of modifier provides change in defined values as noted below from in-vitro pigskin:

ΔL of from 0 to 6 L units, (preferably 0 to 4 L units), wherein said L units are defined by Hunter Lab Color Meter;

change of reflectance of 0.1 to 110% (preferably 0.5 to 95%) as defined by change in gloss measured by a gloss meter;

change in opacity of 0 to ±15%, preferably 0.1 to ±14%, measured in opacity contrast defined by ΔL divided by 60;

wherein Δa* and Δb* are of any value.

In another embodiment, the invention relates to method of enhancing in-use moisturization using a deposition system wherein >50%, preferably 60 to 100% particles are individually coated such that they attach to bubbles/foam formed during dilution/rinse to form a foam/particle structure and >50%, preferably >60% of particles are deposited from the foam portion of foam and liquor fractions formed during rinse.

In another embodiment, the method relates to a method of enhancing smooth skin after-feel using said above-identified deposition system.

EXAMPLES

Protocol

In Vitro Porcine/Pig Skin Assay

A piece of black porcine skin is used (L=40±3), where skin has dimensions of 5.0 cm by 10 cm, and the skin is mounted on black background paper card. Initial measurements of untreated skin are made. The mounted skin is then washed and rinsed with 0.2 g of liquid wash-off formulation or soap bar. After two (2) hours of drying, final measurements are made.

Color Measurements

Initial and final color measurements were made of porcine or in-vivo human skin using a Hunter Lab spectra colormeter using a 0° light source and 45° detector geometry. The spectra colormeter was calibrated with the appropriately black and white standards. Measurements were made before and after wash treatment. Three measurements were made each time and averaged. Values of L, a*, and b*, which came from the L a* b* color space representation, were obtained in this manner. L measures units of "Lightness", a* measures values from red to green and b* measures values from yellow to blue.

Reflectance (Gloss) Determination

Initial and final reflectance/radiance measurements of porcine or in-vivo human skin was made with a glossmeter which measures units of gloss. The glossmeter was first set with both detector and light source at 85° from normal. The glossmeter was calibrated with appropriate reflection standard.

Measurements of gloss were taken before and after application of formulation and Δ gloss was calculated to obtain percent difference.

Opacity Determination

Opacity of washable deposition was calculated from Hunter Lab color measurements. Opacity contrast was calculated from ΔL (change in whiteness after deposition compared to prior to deposition) divided by 60 (which is the difference in L value of skin and a pure white color).

Method to determine partition of Particle in Liquor/Foam Phase (i.e., how much of optical particles is in liquor and how much is in foam):

100 g. of 1% Soap solution was made by dissolving soap shaving on Stirrer bar (~15-20 Minutes). The solution was transferred to a separating funnel and the lather was generated by shaking the separating funnel for 20 times. The foam/liquor phases were allowed to separate for about 30 seconds, and they were drained in separate beakers. The particles were filtered from each layer by filtering through 1.2μ tare filter paper under vacuum. All soluble materials were removed by washing the particles with hot water, and then hot alcohol. The filter paper was dried in vacuum oven @45° C. over night.

The weight fraction of the particles in each phase was then determined by weighing on analytical balance.

Protocol for Squeeze Force Test (Quantification of Cushioning and/or Lubricating Behavior):

Handwash (for generating lather to be measured in squeeze force test):

Handwash under tap water @ room temperature.

Wet the bar; rotate in water 10 times; rotate in hands 12 times.

Collect lather; measure total weight and density.

Squeeze Test:

Test Type

Parallel plate geometry (ARES Rheometer) was used.

Test Type: Multiple Extension Mode Test in Predefined Test Setup using strain controlled in transient mode.

Experimental Conditions:

The initial gap set between parallel plates was 2.0 mm

The $1^{st}$ time zone is the initial experimental time duration, that is 2 seconds (i.e., the distance between two plates going from starting or initial position (2 mm) to final position (0.238 mm) is traveled in 2 seconds), measured using a constant Hencky ratio of −1.0.

As noted, Hencky ratio (1/s, Δd/Displacement×1/time=constant) was used to apply constant rate of strain to the tested sample and the test was used to determine squeeze flow. Linear displacement rate is adjusted to maintain a constant sample strain rate. Hencky ratio is in logarithmic scale, so that Hencky ratio of −1=1/10 or 10% displacement.

The test is used to measure the extensional modulus and properties in samples such as lubrication/cushioning.

The $2^{nd}$ time zone was 30 seconds (during which experimental data is collected) with Hencky ratio of 0 in order for sample to reach equilibrium; the normal force remains almost constant during this period.

In essence, the lather/bubbles are placed between 2 parallel plates and force is applied onto upper plate downward against lather (as noted above). The resistance of the lather to compression is an indication of the perceived “lubrication” of the foam to the consumer, e.g., more resistance is correlated with enhanced lubricating.

Acoustic Rinse Test

Background:

The test involves the use of sound recording to report the contact mechanic events that occur during skin to skin contacts. The acoustic instrument detects skin vibration signals and the sound emission generated during rinsing events. This technique is use to correlate these events to tactile perception. This correlation is based on the acoustic spectra that is generated to provide a tactile impression. These physical signals passing through skin affect consumer perception.

Acoustic Rinse Protocol:

Wet the bar and the forearm in the water tank. Rub the bar on the forearm in circular motion (10-X). Generate the lather on the forearm using similar motion with other palm (10-X). Collect the acoustic signals while rinsing the arm by dipping in the water tank.

Example for Bars

Formulations for bar referred to as Comparatives, A-D and Examples 1-4 are set forth below.

Comparative A

| Ingredient | Function | By Weight |
|---|---|---|
| Polyethylene glycol - 8K | Hydrophilic structurant | 43.5% |
| Cocoamidosulfosuccinate | Anionic surfactant | 30% |
| Fatty Acid | Structurant | 10% |
| Sunflower Seed Oil | Oil | 10% |
| Merquat ® cationic | Cationic | 1.5% |
| Water | | To balance |
| TCM (titania coated mica) | Optical modifier | 5% |

Example 1

| Ingredient | Function | By Weight |
|---|---|---|
| Sugar (e.g., sucrose) | Hydrophilic structurant | 45% |
| Maltodextrin | Hydrophilic structurant | 15% |
| Sodium Laurate | Anionic surfactant | 15% |
| Sodium dodecyl sulfate | Anionic surfactant | 2% |
| Merquat ® cationic | Cationic | 0.4% |
| TCM (titania coated mica) | Optical modifier | 5% |
| $H_2O$ | | to balance |

Comparative B—same as Example 1, but with 10% bismuth oxychloride dispersed in/emulsified in castor oil (70% solids), instead of TCM.

Comparative C—same as Example 2, but with 5% bismuth oxychloride dispersed in/emulsified in castor oil (70% solids), instead of TCM Example 2

| Ingredient | Function | By Weight |
|---|---|---|
| 85/15 Tallow/PKO noodles | Fatty acid soap (cleanser) | 67.61 |
| Merquat 100 or alternative | Cationic polymer | 0.69 |
| Mica - TCM | Optical modifier | 5.00 |
| Sugar | Structurant | 5.00 |
| Glycerin | Humectant | 1.00 |
| PEG | Humectant | 2.00 |
| Sunflower | Oil | 2.00 |
| Perfume | Emotive | 1.50 |
| Water | | To balance |

Example 3

Same as Example 2, Except with 5% TCM Treated with Metal Soap (Al-myristic)

Example 4

| Ingredient | % by wt. |
|---|---|
| Soap (85/15 tallow/palm kernel oil) | 68.00 |
| Glycerin | 1.50 |
| Sunflower oil | 4.00 |
| Mica (Timiron MP-115) ® | 5.00 |
| Glycerin Monostearate | 1.50 |
| Cationic (Merquat 100) | 3.50 |
| CTAC (cetyl trimethylammonium chloride) | 0.50 |
| Water | To balance |
| Perfume and other minors | ~1.50 |

Comparative D—(comparative control): 5% TCM in 85/15 tallow/palm kernel oil soap.

Results of Optical Effects from Deposition

TABLE 1

| | Optical effect from examples | | | |
|---|---|---|---|---|
| | ΔL | | % Δ Gloss | |
| Examples | Direct Contact | Lather Contact | Direct Contact | Lather Contact |
| A (Comparative) | 3.4 | 1.8 | 62.2 | 19.2 |
| 1 | 2.6 | 8.6 | 15.0 | 74.7 |
| B (Comparative) | 1.5 | 3.2 | 110.8 | 41.9 |
| C (Comparative) | 10.4 | 5.2 | 93.6 | 45.0 |
| 2 | 1.1 | 2.8 | 15.1 | 77.2 |
| 3 | 2.18 | 8.20 | 44.0 | 103 |
| 4 | 1.4 | 2.5 | 14 | 65 |
| D (Comparative) | 0.4 | 0.4 | 0.7 | 1.7 |

Generally, working examples are those where most of optical effect is seen from lather contact (deposition from foam/particle structure) rather than from direct contact (e.g., as floc).

Comparative D (Comparative) shows no deposition (very little gloss or L change) because it has no deposition chemistry or hydrophilic structurants.

Example 1 (Sugar, TCM, cationic) shows very high gloss values, indicating good deposition efficiency and shine/radiant effects. The deposition is coming from predominately lather contact over direct product contact. Visual and quantitative evaluation show the TCM is predominately carried in the foam/lather when using the product (see next section and FIG. 4). Microscopic observations show particles are not floced but individually dispersed/suspended (see FIG. 3). It does not show the negative effects of direct contact, such as deposition on the palms of the hands.

Comparatives A, B and C show very high gloss values, indicating good deposition efficiency and shine/radiant effects. The deposition is coming from predominately direct product contact over foam/lather contact. Microscopic observations show particles are floced and not individually dispersed/suspended (see FIG. 2). In visual and quantitative evaluation, the TCM is predominately transferred/deposited via direct contact when using the product. Very little TCM is seen in the foam/lather (see next section). It does show the negative effects of direct contact, such as deposition on the palms of the hands These four examples (1 and Comparatives A-C) show that deposition chemistry and hydrophilic structuring is critical for good deposition, but having the deposition coming from the foam/lather is critical (which only Example 1 shows).

Examples 2, 3, and 4 show very high gloss values, indicating good deposition efficiency and shine/radiant effects. The deposition is coming from predominately lather contact over direct product contact. Microscopic observations show particles are not floced but individually dispersed/suspended (see FIG. 3). In visual and quantitative evaluation, the TCM is predominately carried in the foam/lather when using the product (see next section and FIG. 4). It does not show the negative effects of direct contact, such as deposition on the palms of the hands. Example 2 shows higher gloss values than Example 4 because of use of hydrophilic structurants in the formulation. Example 3 has higher gloss values because of higher deposition efficiency from the foam/lather (more TCM in foam/lather, see next section) due to the use of metal soap treatment.

Example 5

Distribution of TCM During Use of Examples and Deposition Characteristics

Figure 5:
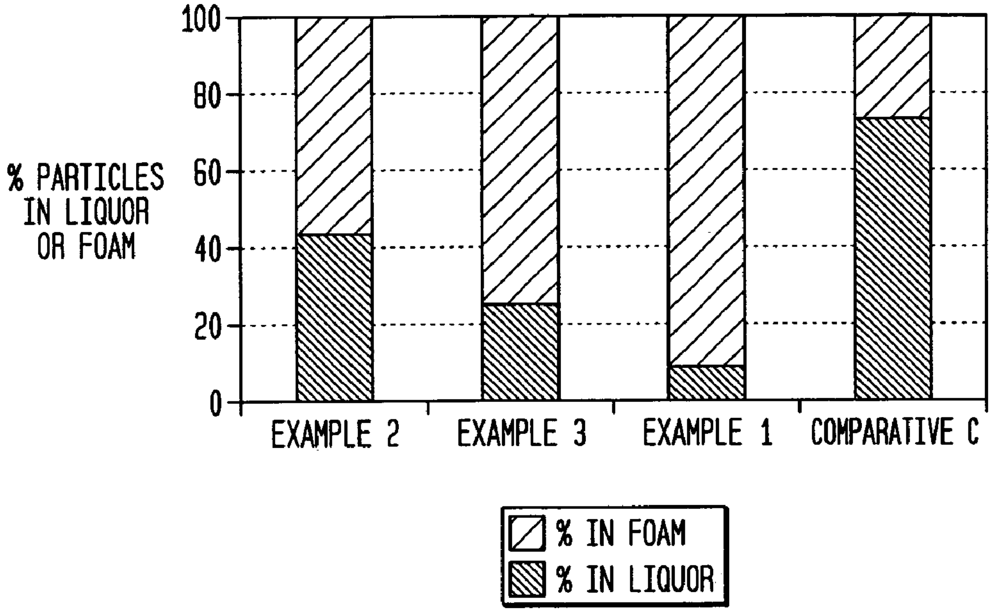
FIG. 5 is table/figure showing how particles, depending on bar composition, will partition predominantly in the foam portion (Examples 2, 3 and 1) or in the liquor portion (Comparative C).

In general (when looking at Examples 1, 2, 3 and Comparative C in FIG. 5), it can be seen that the more hydrophilic structuring, correct surface treatment with deposition chemistry, the more material the foam lather holds. Note, as seen in FIG. 5, Comparative C has a low amount of material in the foam/lather Example 6

Figure 6:
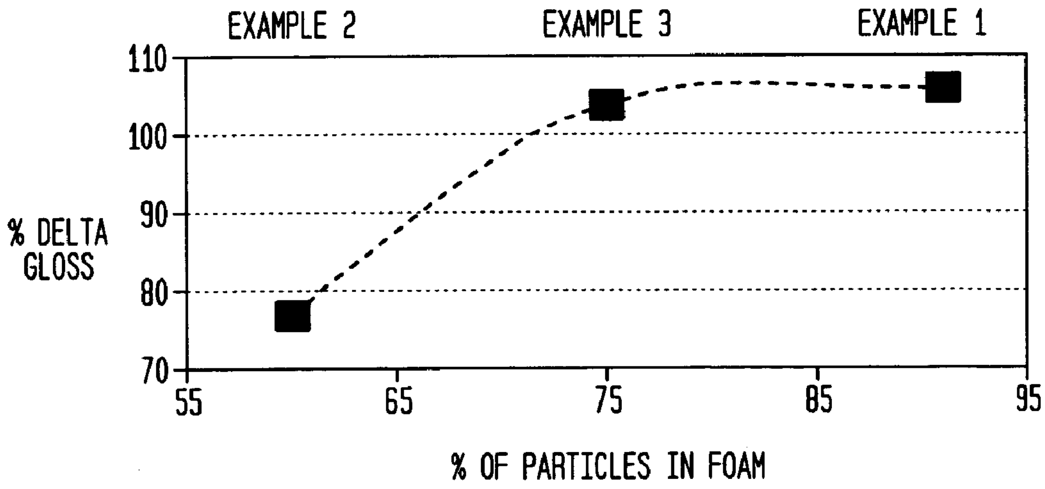
FIG. 6 is graph showing relationship of amount of particles in foam to visual gloss effect from foam/lather deposition.

FIG. 6 shows the relationship of amount of particles in foam to visual gloss effect from foam/lather deposition. More material (TCM) in the foam/lather, the higher the gloss of the deposition (more TCM deposited). Note, because Comparative C has a low amount of TCM in the foam/lather, the resulting shine/gloss change is less (less material deposited) and not plotted on the graph.

Example 7

In-Use Moisturization Feel and Smooth Skin after Feel Characteristics

Figure 7:
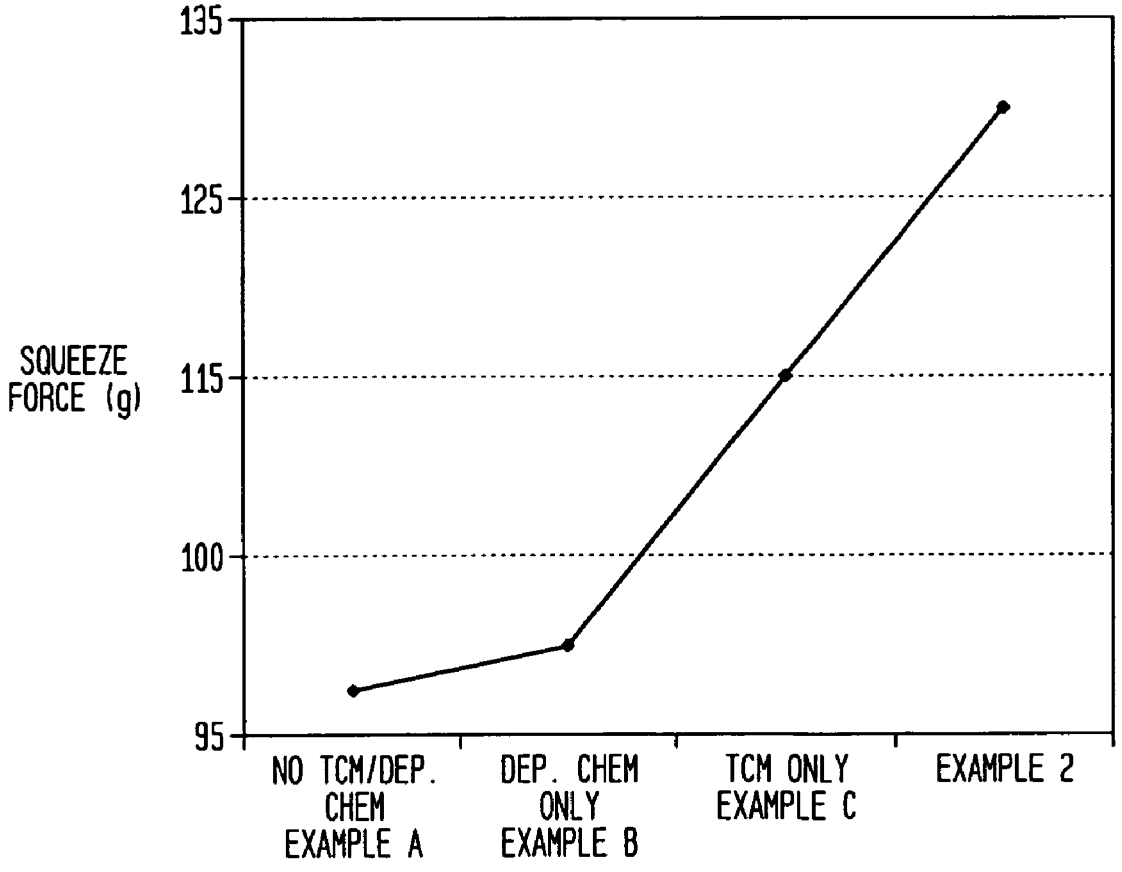
FIG. 7 is graph showing relation of foam particle deposition and moisturization.

FIG. 7 shows the squeeze force of the foam/lather for Example 2 and the effect of the key components. Example A is Example 2 but without the TCM or the deposition chemistry (cationic polymer, PEG, etc.). Example B is Example 2 without the TCM, but with the deposition chemistry. Example C is Example 2 without the deposition chemistry, but with the TCM. The importance of the squeeze force in foam/lather is that the higher the squeeze force value, the cushionier and moisturizing feel the lather/foam has.

As seen from FIG. 7, Examples A and B have effectively the same value. This means that the deposition chemistry by it's self does not give the moisturizing lather/foam feel. Example C has a significant increase in squeeze force indicating that the flat platy TCM does contribute to the moisturizing feel of the foam/lather. The flat platy TCM particles are being incorporated into the foam/lather, forming a structure, which increases the squeeze flow. Example 2 has the highest squeeze force value of all the examples (much higher than Example C). This shows a non obvious synergistic effect of the flat platy TCM, with the deposition chemistry coated on its surface, creating a foam/lather structure which has a moisturizing lather/foam feel.

Example 8

Smooth Skin after Feel and Deposition.

Figure 8:
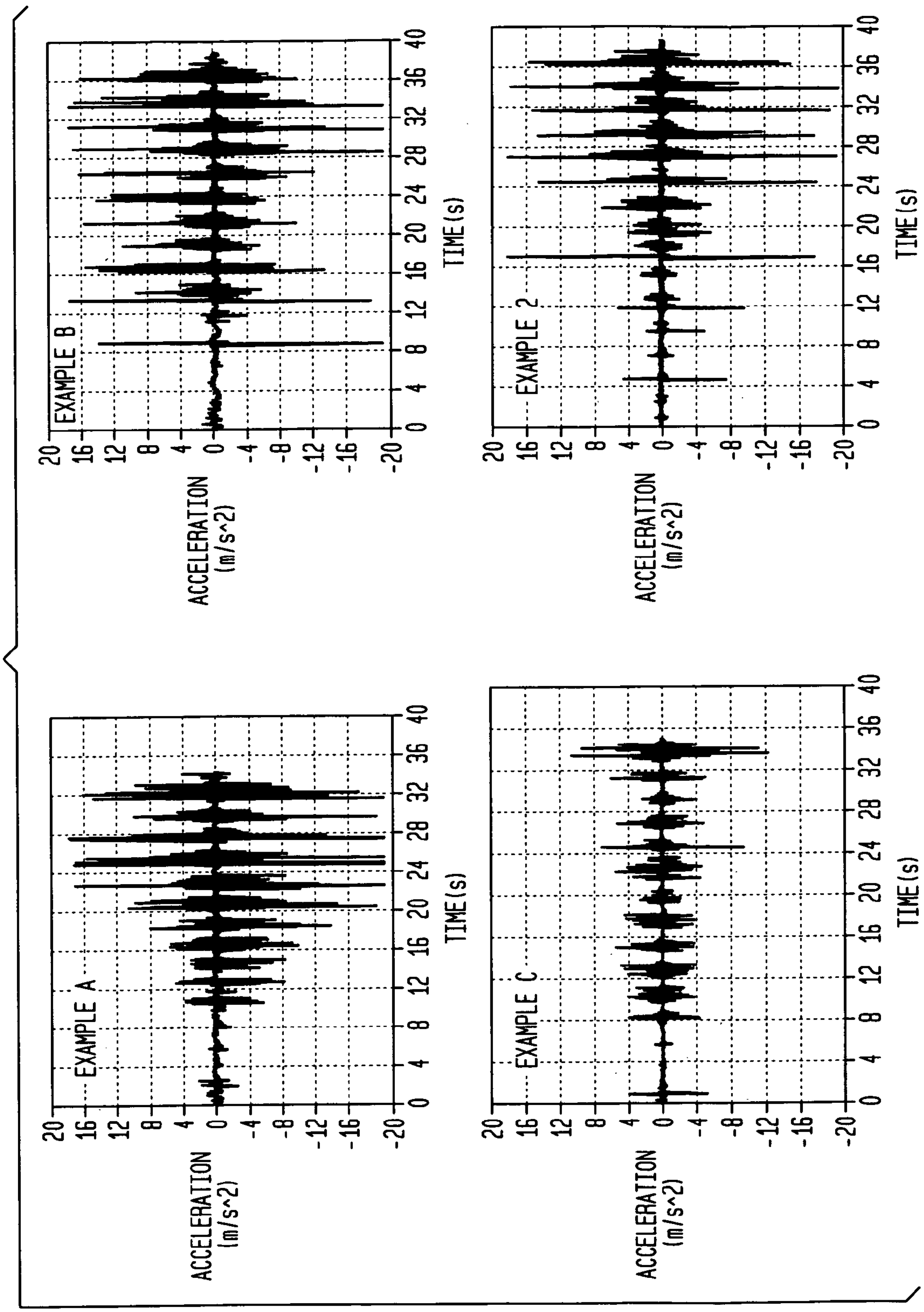
FIG. 8 is acoustic analysis showing effect of flat platy TCM with deposition chemistry (e.g., cationic polymer/anionic surfactant) coated on surface.

Using the examples of the previous section, the effects of Example 2 components on smooth skin after feel are seen. The acoustical patterns (in FIG. 8) show how smooth the skin feels from the friction noise.

Example A (no TCM and no deposition chemistry) and B (only deposition chemistry) shows no significant difference in acoustical patterns. Example C shows an amplitude attenuation (from ±12 in Examples A and B to ±4 in example C) of the friction noise, which shows a degree of smooth skin after feel. Example 2 shows a significant change in the acoustical pattern. It shows not only amplitude attenuation as in Example C but also the delay time of amplitude friction noise, with values of ≧±4 (all of the examples show a delay time ~8 sec, while Example 2 has a delay time of ~24 sec.), is increased. This is a non obvious and synergistic effect of the flat platy TCM with the deposition chemistry coated on its surface.

We claim:

1. A bar composition consisting of:

(a) 5 to 90% by wt. of a surfactant system comprising a surfactant or surfactants selected from the group consisting of soap, alkyl sulphate and mixtures thereof, (b) 20 to 80% by wt. water-soluble or water insoluble hydrophilic structurant comprising sugar;

(c) 0.1 to 20% by wt. of deposition enhancement system comprising 0.1 to 1% of a cationic polymer having charge density of ≧6.2 Meg/gm and 0.1 to 30% by wt, anionic surfactant selected from the group consisting of $C_{10}$-$C_{24}$ fatty acid soap, alkyl sulfate and mixtures thereof;

wherein molecule or molecules forming said deposition enhancement system form an individual coating in situ on about 50% to 100% of flat platy titania coated mica optical modifier particles in said composition, thereby allowing said optical modifier particles to attach individually on foam bubbles formed during rinse dilution or use and to deposit said particles from a foam/particle structure also formed during said rinse;

(d) 0 to 10% by wt. oil/emollient at least some of which emollient molecules may be present as part of the in-situ coating deposition system;

(e) 1 to 5% hydrophilic emollient selected from the group consisting of glycerin, polyalkylene glycol, trialkanolamine, urea and mixtures thereof;

(f) 0.1 to 15% by wt. solid particulate titania coated mica optical modifier particles, wherein said modifier particles comprises flat platy particulates having D50 size range of 6 to 70 micrometer and thickness to 50 to 1000 nanometer, said particles being the substrate for the in-situ deposition enhancement system of (c); and (g) 1 to 20% water, wherein from at least 50% to 100% of platy particles present in the composition deposit onto skin or other substrate from the foam portion of a foam portion and liquor portion generated during rinse.

2. A composition according to claim 1, comprising 10 to 60% by wt. surfactant.

3. A composition according to claim 1, wherein said particulate optical modifier of (f) is delivered to skin from said foam/particle structure of (c).

4. A composition according to claim 1 comprising 20 to 70% by wt. structurant.

5. A composition according to claim 1, wherein an integral structure with the foam/lather is formed to create a deposition vehicle upon dilution.

6. A composition according to claim 5, wherein the deposition vehicle can be broken upon shear or rubbing to form a uniform and dispersed film on surface of skin.

7. A composition according to claim 1, wherein the cationic or one of the cationic polymers is Merquat 100.

8. A composition according to claim 1, wherein said emollient further aids deposition of optical modifier.

9. A composition according to claim 1, comprising 0.5 to 10% optical modifier particles.

10. A composition according to claim 1, providing change in radiant luminosity wherein delivery of modifier provides change in defined values as noted below from in-vitro pigskin:

ΔL of from 0 to 6 L units, (preferably 0 to 4 L units) wherein said L units are defined by Hunter Lab Color Meter;

change of reflectance of 0.1 to 110% (preferably 0.5 to 95%) as defined by change in gloss measured by a gloss meter;

change in opacity of 0 to ±15% measured in opacity contrast defined by ΔL divided by 60;

wherein Δa* and Δb* are of any value.

11. A composition according to claim 1, wherein said platy optical modifier is a non colored or colored organic or inorganic material selected from organic pigments; inorganic pigments; polymers and fillers in turn selected from:

i) coated mica or platy organic or inorganic substrate, coated with one or multiple layers of titanium oxide, iron oxide, chromium oxide, metal oxides/mixed metal oxides, nitrides, sulfides, carbides, or mixtures thereof;

ii) platy single crystals such as bismuth oxychloride, boron nitride, aluminum oxide, calcium sulfate, iron oxide, mixed metal oxides, metal oxides, nitrides, sulfides, halides, or mixtures thereof;

iii) platy silicate materials(natural or man made) such as mica, talc, sericite, flouromica, platy silicon oxide, platy borosilicate and platy glass, or mixtures thereof;

iv) a mixture of some or all of the groups above.

12. A composition according to claim 1, said platy optical modifier is defined as follows:

(a) exterior surface with refractive index of 1.3 to 4.0;

(b) thickness of 50 nm to 1,000 nm, preferably 100 nm to,1000 nm; and (c) $D_{50}$ of 6 to 70 microns in particle size, preferably 14 to 35 microns.

13. A composition according to claim 11 wherein the materials of (i), (ii), (iii) and/or (iv) contain inorganic or organic material capable of generating color.

14. A composition according to claim 12, wherein said modifier is further defined by a color obtained by fluorescence, absorption and/or interference.

15. A composition according to claim 11, wherein optical particle contain surfactant modifier selected from amino acids, proteins, fatty acids, lipids, phospholipids, anionic and/or cationic oligomers/polymers and mixtures thereof.

16. A method of enhancing in-use moisturization feel using compositions of claim 1.

17. A method of enhancing smooth skin after-feel using compositions of claim 1.

* * * * *